US008647681B2

(12) United States Patent
Markwell et al.

(10) Patent No.: US 8,647,681 B2
(45) Date of Patent: Feb. 11, 2014

(54) SKIN DIET

(75) Inventors: Peter John Markwell, Melton Mowbray (GB); Timothy Richard Fray, Leicestershire (GB)

(73) Assignee: Mars, Inc., McLean, VA (US)

( * ) Notice: Subject to any disclaimer, the term of this patent is extended or adjusted under 35 U.S.C. 154(b) by 773 days.

(21) Appl. No.: 10/479,065

(22) PCT Filed: May 31, 2002

(86) PCT No.: PCT/GB02/02538
§ 371 (c)(1),
(2), (4) Date: Jun. 1, 2004

(87) PCT Pub. No.: WO02/096221
PCT Pub. Date: Dec. 5, 2002

(65) Prior Publication Data
US 2004/0241286 A1 Dec. 2, 2004

(30) Foreign Application Priority Data
Jun. 1, 2001 (GB) .................................. 0113348.7

(51) Int. Cl.
A61K 36/00 (2006.01)
(52) U.S. Cl.
USPC .......................................................... 424/725
(58) Field of Classification Search
None
See application file for complete search history.

(56) References Cited

U.S. PATENT DOCUMENTS

| | | | |
|---|---|---|---|
| 4,602,004 A | 7/1986 | Cohen | |
| 4,629,625 A * | 12/1986 | Gaull | 424/643 |
| 4,681,896 A | 7/1987 | Horrobin | |
| 4,704,280 A | 11/1987 | Bates | |
| 4,725,438 A * | 2/1988 | Leazer | 424/744 |
| 4,777,162 A * | 10/1988 | Hijiya et al. | 514/58 |
| 4,806,569 A | 2/1989 | Horrobin | |
| 4,868,212 A | 9/1989 | Horrobin | |
| 5,449,517 A | 9/1995 | Fitzjarrell | |
| 5,468,737 A | 11/1995 | McAnalley et al. | |
| 5,567,732 A * | 10/1996 | Kyle et al. | 514/560 |
| 5,629,002 A | 5/1997 | Weuffen et al. | |
| 5,643,623 A * | 7/1997 | Schmitz et al. | 426/73 |
| 5,763,484 A | 6/1998 | Horrobin | |
| 5,824,659 A | 10/1998 | Strickland et al. | |
| 5,925,357 A * | 7/1999 | Cerqueira et al. | 424/744 |
| 5,976,559 A * | 11/1999 | De Lacharriere et al. | 424/401 |
| 5,989,604 A * | 11/1999 | Wolf et al. | 426/103 |
| 6,007,861 A * | 12/1999 | Von Lempke | 426/412 |
| 6,117,477 A * | 9/2000 | Paluch | 426/623 |
| 6,127,409 A | 10/2000 | Suzuki et al. | |
| 6,136,339 A * | 10/2000 | Gardiner | 424/439 |
| 6,159,508 A * | 12/2000 | Wolf et al. | 426/2 |
| 6,168,802 B1 * | 1/2001 | Howard et al. | 424/439 |
| 6,210,701 B1 * | 4/2001 | Darland et al. | 424/439 |
| 6,228,402 B1 | 5/2001 | Wolf et al. | |
| 6,296,880 B1 * | 10/2001 | Murad | 424/616 |
| 6,333,063 B2 * | 12/2001 | Ariga et al. | 426/656 |
| 6,521,271 B1 * | 2/2003 | Phan | 424/756 |
| 6,673,843 B2 * | 1/2004 | Arbiser | 514/679 |
| 6,737,089 B2 * | 5/2004 | Wadsworth et al. | 424/777 |
| 2002/0132800 A1 * | 9/2002 | Popp et al. | 514/168 |

FOREIGN PATENT DOCUMENTS

| | | | |
|---|---|---|---|
| AU | 200056540 | | 3/2001 |
| CN | 1240146 | | 1/2000 |
| CN | 1272324 | | 11/2000 |
| CN | 1272340 | | 11/2000 |
| DE | 4316293 | | 5/1996 |
| DE | 19910697 A1 | * | 9/2000 |
| EP | 0115419 A2 | | 8/1984 |
| EP | 0440307 A2 | | 8/1991 |
| EP | 0440308 A1 | | 8/1991 |
| EP | 0440309 A1 | | 8/1991 |
| EP | 0115419 B1 | | 4/1992 |
| EP | 0440307 B1 | | 8/1994 |
| EP | 0440309 B1 | | 8/1994 |
| EP | 0678247 | | 10/1995 |
| EP | 0875514 | | 11/1998 |
| JP | 63-211216 | | 9/1988 |
| JP | 63211216 A | * | 9/1988 |
| JP | 7277939 | | 10/1995 |
| JP | 9030987 | | 2/1997 |
| JP | 9143063 | | 6/1997 |
| JP | 2000083620 | | 3/2000 |
| JP | 2000-290189 | | 10/2000 |
| JP | 2000290189 | | 10/2000 |
| JP | 2000290189 A | * | 10/2000 |

(Continued)

OTHER PUBLICATIONS

Watson, T. "Diet and Skin Disease in Dogs and Cats," Journal of Nutrition: 128: 2783S-2789S, 1998 (7 pages total).*
Gura; Science; (1997) vol. 278, pp. 1041-1042 (2 pages total).*
D. P. LaFlamme, Determining metabolizable energy content in commercial pet foods, Journal of Animal Physiology and Animal Nutrition, Dec. 20, 2001, pp. 222-230, vol. 85 Issue 7-8, Blackwell Verlag GmbH, published online.
Dorland's Illustrated Medical Dictionary; 2000; pp. 741-742; pp. 1651 and 1653; 29th Edition; W.B. Saunders Company; Philadelphia, PA.
Klein et al, "Aloe Verra," Journal of American Academy of Dermatology, vol. 18, 1988, pp. 741-720.
Lobo et al, "Taurine Levels and localisation in the stratified squamous epithelia," Histochem Cell biology, vol. 115, 2001, pp. 341-347.

(Continued)

Primary Examiner — Amy L Clark
(74) Attorney, Agent, or Firm — Norton Rose Fulbright LLP

(57) ABSTRACT

The present invention provides a foodstuff comprising vitamin C, taurine, curcumin and *aloe vera*, it use in the control of skin disorders and methods for controlling skin disorders. The foodstuff of the invention assists in the management of a skin disorder such as inflammatory or allergic skin disorders. The foodstuff further assists in the management of secondary infections associated with the skin disorder. Use of the foodstuff may allow the reliance on conventional treatments for skin disorders to be reduced.

11 Claims, 9 Drawing Sheets

(56) References Cited

FOREIGN PATENT DOCUMENTS

| | | |
|---|---|---|
| WO | WO 9212699 | 8/1992 |
| WO | WO-9518606 | 7/1995 |
| WO | WO-9809635 | 3/1998 |
| WO | WO-9918814 | 4/1999 |
| WO | WO 9942101 A1 * | 8/1999 |
| WO | WO-9948381 | 9/1999 |
| WO | WO 0070949 A1 * | 11/2000 |
| WO | WO-02096221 | 12/2002 |

OTHER PUBLICATIONS

Eady et al, "Spotting the onset of puberty—the secret's in the skin," Microbiology Today vol. 28, Nov. 2001.

Muller et al, "Acne," Small Animal Dermatology Third Edition, 1983.

Fray et al., "A combination of aloe vera, curcumin, vitamin C, and taurine increases canine fibroblast migration and decreases tritiated water diffusion across canine keratinocytes in vitro," *J. Nutr.*, 134:2117S-2119S, 2004.

* cited by examiner

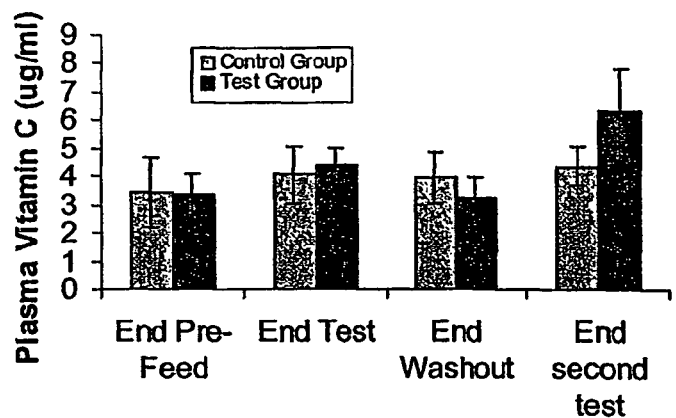
Figure 1. Concentrations of plasma vitamin C at the end of each stage in the trial, for the test and control groups.
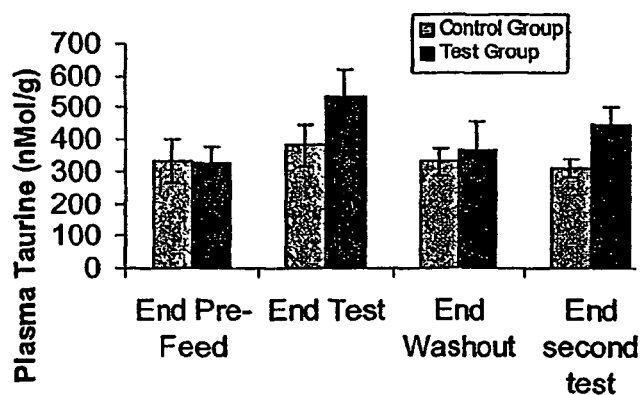
Figure 2. Concentrations of plasma taurine at the end of each stage in the trial, for the test and control groups.

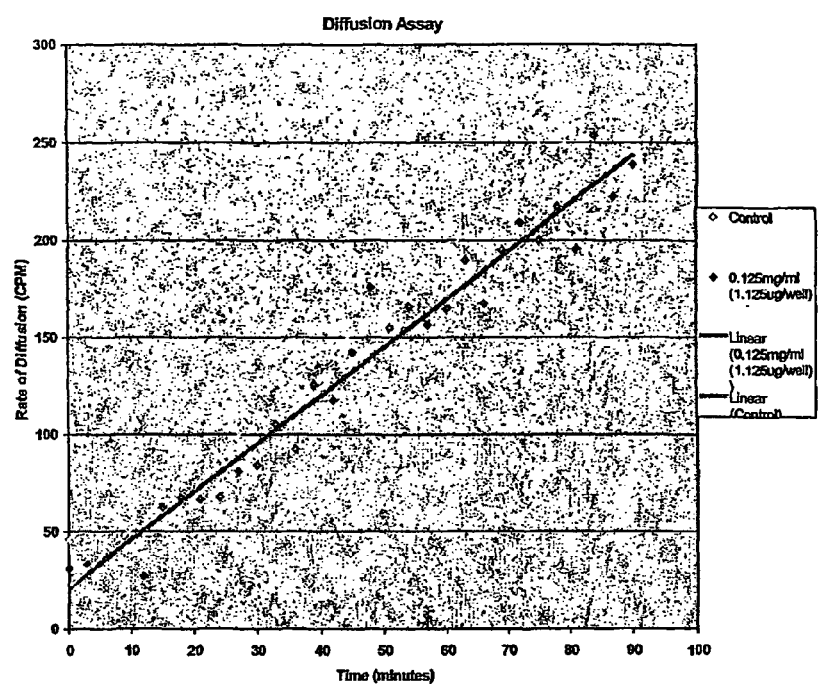
Figure 3. Diffusion assay results for living skin equivalents cultured with and without foodstuff. Lines of linear regression have been fitted to the control data (yellow) and the test data with the foodstuff (red).

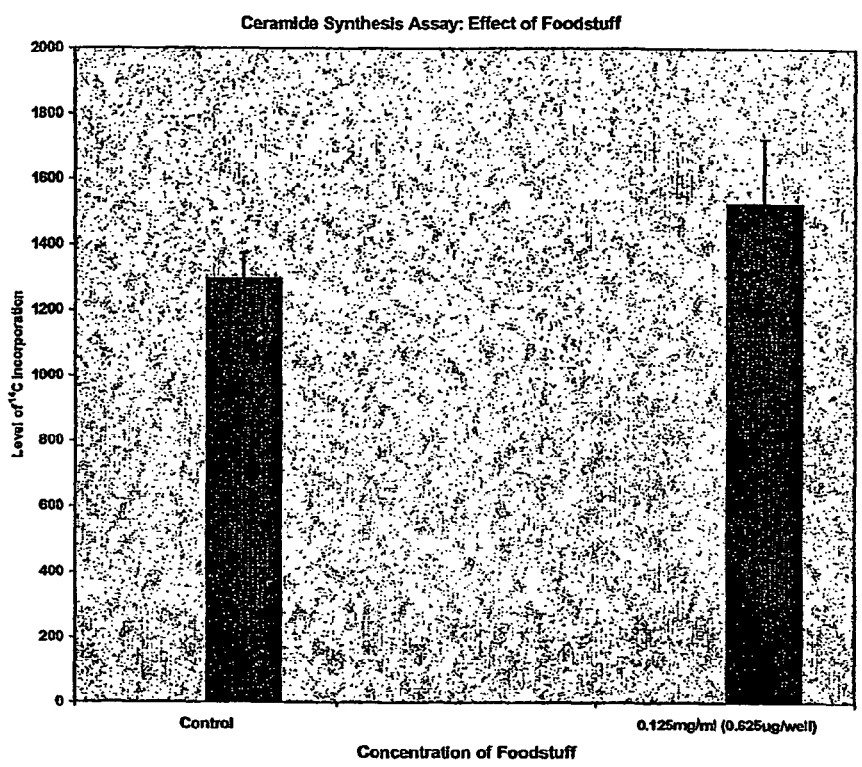
Figure 4. Graph showing the effect of 0.125 mg/ml of foodstuff on keratinocyte skin lipid production.

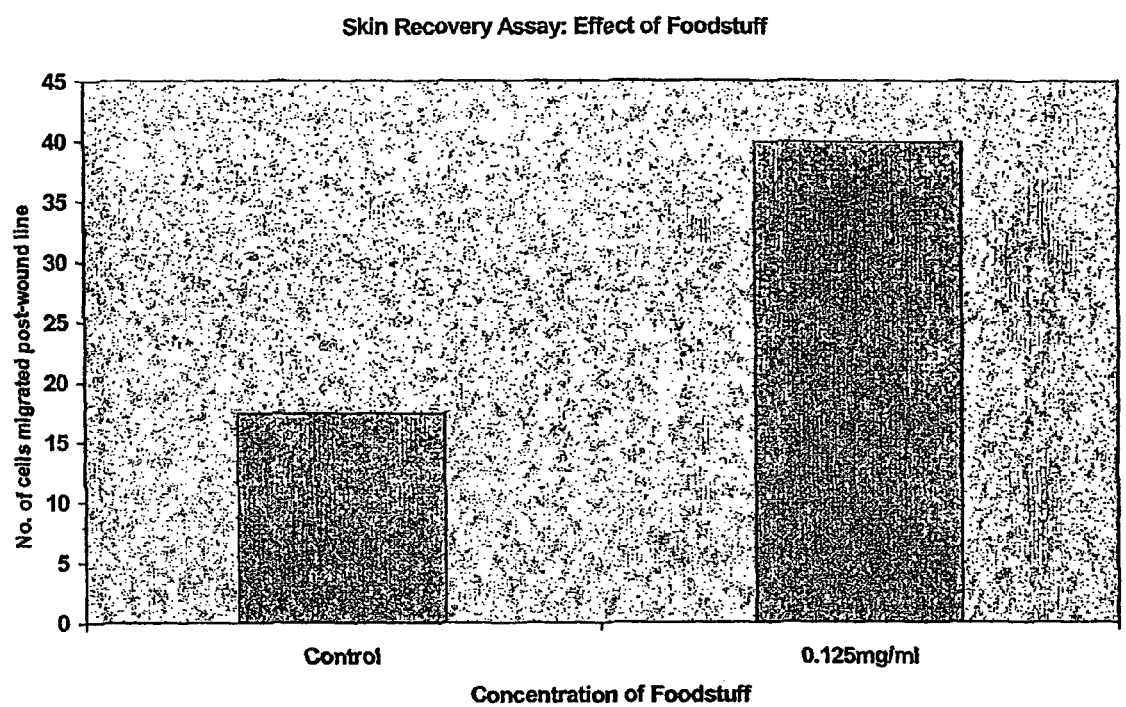
Figure 6. Graph showing the mean number of fibroblasts migrated past the wound line during the skin recovery assay with and without foodstuff (0.125mg/ml).

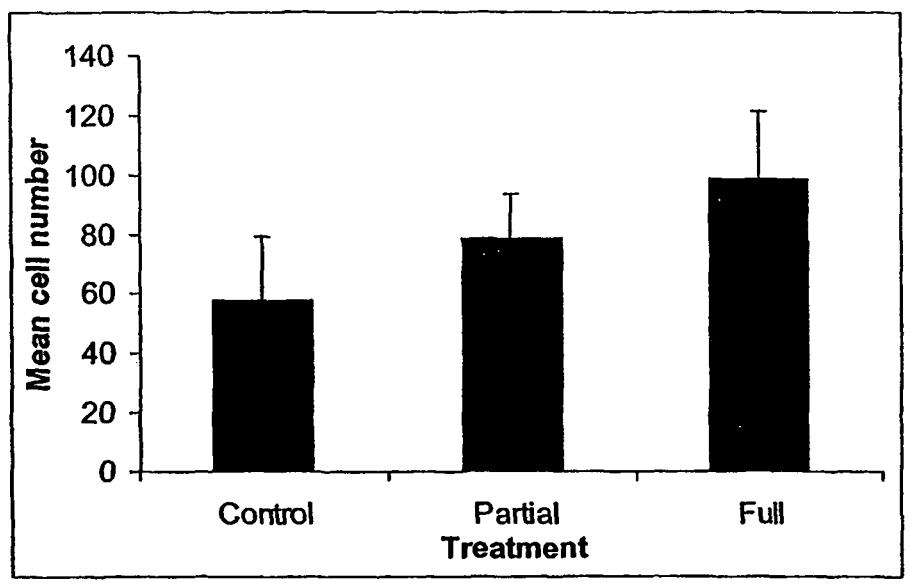
Figure 7 Graph showing mean number of fibroblasts migrated past the wound line during the skin recovery assay with full and partial foodstuff and without foodstuff (0.125mg/ml).

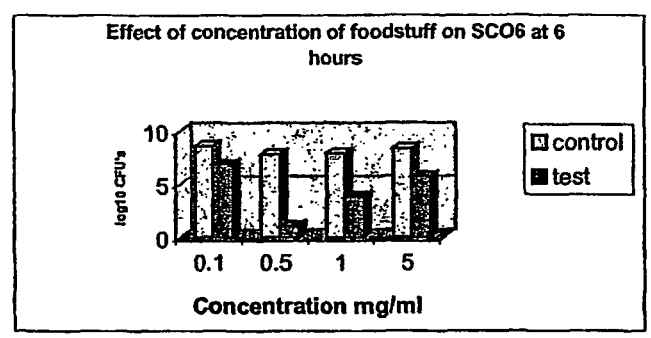
5
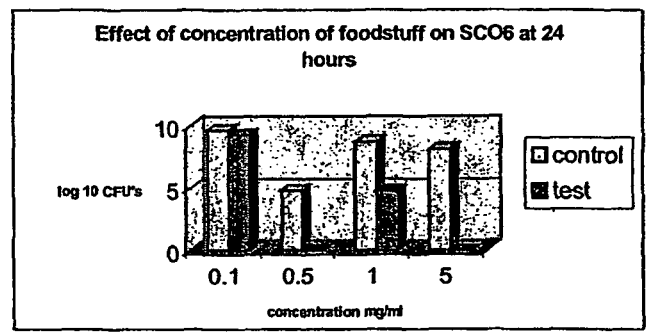
Figure 8 Bacteriocidal effect of foodstuff on SCO6.

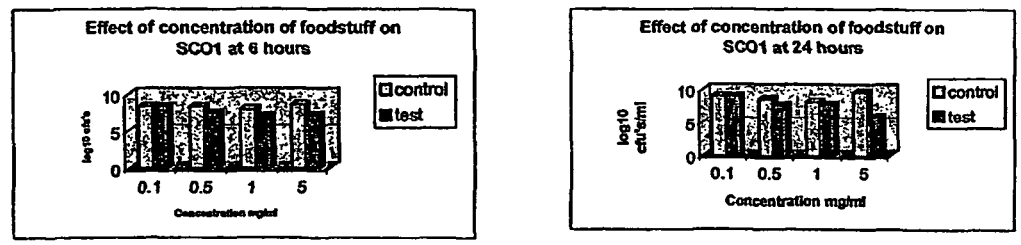
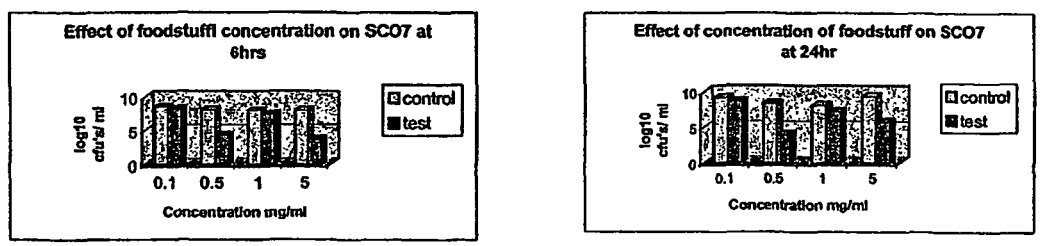
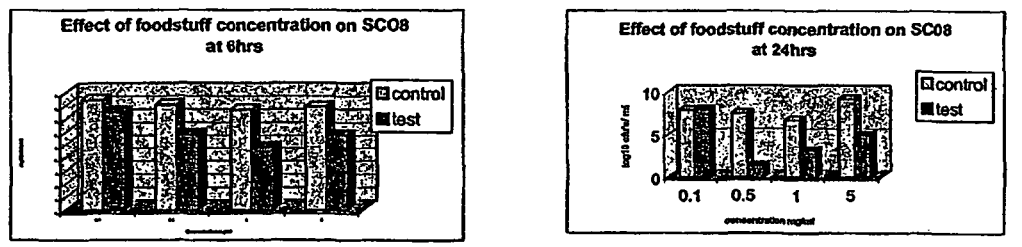
Figure 9 Bacteriocidal effect of foodstuff on isolates from dog coat

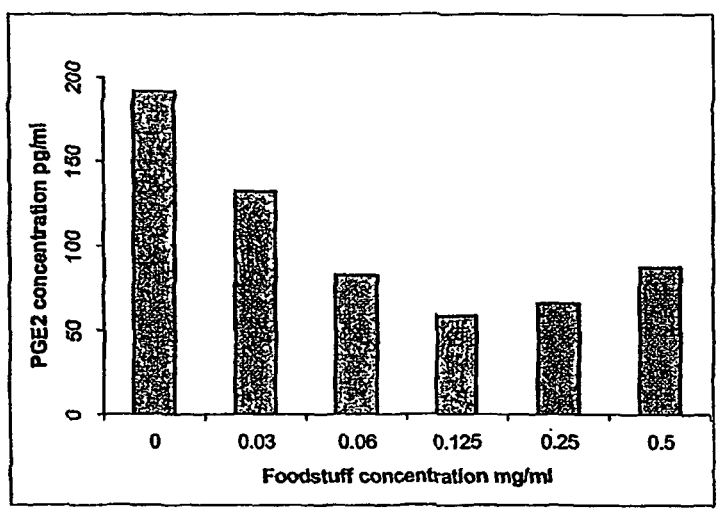
Figure 10. Graph showing the effect of the foodstuff on fibroblast supernatant
PGE2 levels.

SKIN DIET

CROSS-REFERENCE TO RELATED APPLICATIONS

This application is a national stage filing of PCT/GB02/02538 filed May 31, 2002 claiming priority to GB 0113348.7 filed Jun. 1, 2001.

TECHNICAL FIELD

The present invention provides a foodstuff comprising vitamin C, taurine, curcumin and *aloe vera*, its use in the control of skin disorders and methods for controlling skin disorders.

BACKGROUND OF THE INVENTION

The present invention provides a foodstuff comprising vitamin C, taurine, curcumin and *aloe vera*, its use in the control of skin disorders and methods for controlling skin disorders.

In most household pets, a healthy skin and coat indicates an animal in general good health. As the skin and coat condition of a pet provides such an important visual impact (in particular to pet owners and/or to the public in general) it is, an ongoing aim in the art to improve the skin and hair conditions of animals, in particular where an animal suffers from a skin disorder.

Skin disorders such as flea allergy or atopy cause discomfort or distress to an animal. In addition, such disorders reduce the actual or perceived condition of the skin or hair of an animal. It is therefore an aim of this invention to provide a foodstuff, which can be used to assist in the treatment of skin disorders in an animal, particularly in a dog. The provision of a foodstuff to control skin disorders is convenient for the owner as the foodstuff can be administered instead of or in combination with the animal's conventional food. Thus, administration of the foodstuff avoids the inconvenience and distress associated with the use of shampoos or skin ointments, creams or lotions.

Furthermore, the foodstuff of the invention utilizes ingredients which can occur naturally to provide a benefit to an animal. This will overcome any real or perceived disadvantage in treating an animal with drugs, primarily prescription drugs.

BRIEF SUMMARY OF THE INVENTION

The first aspect of the invention provides a foodstuff comprising vitamin C, taurine, curcumin and *aloe vera*.

*Aloe vera* is obtained from *Aloe* sp. plants, which are members of the lily (Liliaceae) family. For the purposes of this invention, *aloe vera* can be obtained from any member of this family, including from one or more of *Aloe barbadensis, Aloe arborescens, Aloe plicatuis, Aloe rahombe, Aloe ferrox, Aloe perryi, Aloe chinensis, Aloe elongata, Aloe indica, Aloe officinalis, Aloe perfoliata, Aloe rubescens, Aloe vera* L. var *littoralis, Aloe vulgaris* or *Aloe saponaria*. *Aloe vera* can be obtained from any part of the *Aloe* plant including the skin, leaf, stem, shoot, bulb, root, fruit, flower or seed. In particular, *Aloe vera* is obtained from the leaf. For the purposes of this invention, *aloe vera* can be provided as whole leaf, a gel (for example a mucilage), a exudate (yellow latex), a juice, a concentrated extract, and/or a freeze dried powder. In addition, *aloe vera* can be provided dried, fresh, crushed, in solution, in oil, as a powder, liquid, (either as a solution or as an oil or juice) or semi solid. Preferably, the *aloe vera* is provided as a freeze dried powder. More preferably the freeze dried powder is substantially free of aloin and *aloe*-emodin.

The *aloe vera* of the first aspect is preferably provided from the outer leaf of the *Aloe* sp. plant. The plant material is treated with one or more enzymes to remove fibrous backbone and/or solid debris. Aloin and *aloe*-emodin is preferably removed from the plant material for example by passing the plant material over charcoal. Preferably the plant material provides less than 20 ppm aloin and less than 10 ppm *aloe*-emodin, more preferably less than 15 ppm aloin and 5 ppm *aloe*-emodin. The powder is then freeze dried. Such a powder comprising 100% active agents is designated a 100% active solid. For the purposes of this invention, the *aloe vera* is preferably provided as a 100% active solid or the equivalent thereof.

*Aloe vera* contains a number of different components, including those summarized below.

| Aloe component | Activity | Effects |
|---|---|---|
| Vitamin A, C and E | Antioxidants | Prevent oxidative stress and damage from free radicals. |
| Carboxypeptidase | Bradykinase inhibitor | Anti-inflammatory and analgesic |
| Elements Na, K, Mg, Ca, Cu, Mn, Cu, Zn and Fe | Magnesium lactate inhibits histamine decarboxylase | Anti-inflammatory, anti-pruritic |
| Long chain polysaccharides | Gut barrier formation and immuno-modulation | Prevents 'leaky gut syndrome' and regulates the immune response. |
| Salicyclic acid | Prevents biosynthesis of prostoglandins, thereby reducing the effects of histamine and serotonin | Anti-inflammatory, analgesic |
| Anthraquinones, Saponins | | Purgative, analgesic, absorb UV, antimicrobial, aids absorption in gut |
| Mannose-6-phosphate | Binds to fibroblasts and simulates IGF action | Improves wound healing and anti-inflammatory |
| Amylase, lipase, aloctin-A | Enzymic degradation of necrotic tissue and stimulation of macrophages | Aid digestion, wound healing |
| Magnesium lactate | Inhibits histidine decarboxylase | Blocks formation of histidine, anti-pruitic |

For the purposes of this invention, the *aloe vera* may provide one or more of the above-listed components. The *aloe vera* provided may contain further components in addition to those listed above, for example phenols, tannic acid etc.

The inclusion of *aloe vera* may provide one or more of the following therapeutic benefits; improvement of collagen repair, prevention of hair loss, anti-inflammatory, anti-irritant, antiseptic, anti-oxidant, reduction of flea irritation, antimicrobial, reduced secondary skin infections and improved recovery from skin disorders.

Throughout this text, references to a concentration per kcal are to kcal total metabolisable energy intake.

*Aloe vera* is provided in the foodstuff of the first aspect at a level (all per 400 kcal) of between approximately 1 mg and approximately 1000 mg, preferably between approximately 10 mg and approximately 500 mg, more preferably between approximately 20 mg and approximately 150 mg, more preferably approximately 40 mg to approximately 90 mg. In a most preferred feature of the first aspect, *aloe vera* is provided at a level of 70 mg or above per 400 kcal. The above levels are provided where *Aloe vera* is a 100% active solid. Where the *aloe vera* is provided in an alternative form, an equivalent amount of *aloe vera* can be provided (for example, for a 50% active solid, approximately twice as much *aloe vera* will be provided in the foodstuff of the first aspect).

The foodstuff of the first aspect comprises vitamin C. Vitamin C is a water-soluble substance which has a number of important roles in the body. It has an essential role in the maintenance of healthy teeth, gums and bones. It aids the healing of wounds, scar tissue and fractures and strengthens blood vessels. Vitamin C also builds resistance to infection and aids in the prevention and treatment of the common cold. Vitamin C is also one of the major antioxidant nutrients.

The vitamin C according to the first aspect of the invention may be in any form. It may be liquid, semi-solid or solid.

Vitamin C for the purposes of this invention is provided at a level (all per 400 kcal) of approximately 20 mg to approximately 500 mg, preferably approximately 150 mg to approximately 400 mg, more preferably at a level of approximately 350 mg or above.

The foodstuff of the first aspect further comprises curcumin. Curcumin is a major component of tumeric (*Curcuma longa*). Curcumin has a number of beneficial activities including inhibition of tumour initiation, anti-inflammatory, anti-oxidant, suppression of mitogen-induced proliferation of blood mono-nuclear cells, inhibition of mixed lymphocyte reaction and inhibition proliferation of smooth muscle cells. In addition, curcumin has immunoglobulin production-regulating activity and has been shown to induce reductions in immunoglobulin E and M and increases in immunoglobulin G. The immunoglobulin regulating activity is useful for treating the inflammation associated with secondary infection, atopy and flea allergy. By reducing the inflammation, the pain associated with this reaction can also be reduced. As a secondary use, by reducing the inflammation, the complex processes involved in recovery can proceed unhindered and with appropriate speed.

Curcumin is provided at a level (all per 400 kcal) of approximately 100 mg to approximately 1000 mg, preferably approximately 200 mg to approximately 800 mg, more preferably at a level of approximately 500 mg or above.

The foodstuff of the first aspect comprises taurine. Taurine is a non-essential amino acid which is obtained from meat and fish. It stimulates the production of glycosphingolipids in the skin by acting as a precursor molecule. Glycosphinogolipids exhibit anti-microbial properties. Taurine is provided in the foodstuff at a level (all per 400 kcal) of from approximately 100 mg to approximately 1000 mg, preferably from approximately 150 mg to approximately 800 mg more preferably approximately 200 mg or above.

The combination of the above ingredients have been shown to provide a benefit in terms of skin health of an animal.

The foodstuff can additionally comprise one or more of vitamin A, zinc or one or more fatty acids (such as polyunsaturated fatty acids).

The polyunsaturated fatty acids may include one or more omega-3 fatty acids (which include eicosapentaenoic acid (EPA), docasahexaenoic acid (DHA) or alpha-linolenic acid (ALA)) or one or more omega-6 fatty acids (which include gamma-linolenic acid (GLA)). Each of the fatty acids may be provided in a purified form or by one or more of fish oil, soya oil, blackcurrent oil, sunflower oil or ground nut oil. The fatty acids can further be obtained from flaxseed.

Polyunsaturated fatty acids are anti-inflammatory and anti-oxidant compounds. They are useful in the treatment of atopy, flea allergic dermatitis and pruritus.

The fatty acids may be provided at levels of approximately 10 mg to approximately 1000 mg per 400 kcal preferably from approximately 50 mg to approximately 500 mg per 400 kcal, more preferably approximately 200 mg per 400 kcal per day or above. Most preferably, eicosapentaenoic acid is provided at a level of approximately 300 mg per 400 kcal or above and/or docasahexaenoic acid is provided at a level of approximately 200 mg per 400 kcal or above.

Zinc is a component of a number of enzyme systems involved in skin and hair growth. The role of the zinc may be associated with the adherence of skin scales and hair scales to each other. In addition, zinc has a role in the immune system.

Zinc may be provided in the foodstuff of the first aspect at a level (all per 400 kcal) of from approximately 5 mg to approximately 50 mg, preferably from approximately 10 mg to approximately 30 mg more preferably approximately 28 mg or above.

The foodstuff further optionally comprises vitamin A or its precursor beta-carotene. Vitamin A has strong antioxidant properties and has been shown to be beneficial against selected cancers, cardiovascular diseases, cataracts and age related macular degeneration. Vitamin A is particularly effective at scavenging peroxyl radicals and is a very potent singlet oxygen quencher at low oxygen tensions. Supplementation of the diet with vitamin A has been reported to reduce lipid peroxidation.

Vitamin A may be provided at a level (all per 400 kcal) of approximately 1000 IU to 10,000 IU, more preferably 2000 IU to 8000 IU, most preferably at a level of approximately 5000 IU per 400 kcal or above.

It is believed (without being bound to this theory) that a combination of zinc, vitamin A and vitamin C stimulate collagen synthesis and are cofactors in the formation of prostaglandin E1. Thus, a preferred feature of the first aspect provides a foodstuff of the first invention comprising vitamin C, taurine, curcumin and *aloe vera* and additionally comprising zinc and vitamin A.

The present invention relates, for all aspects, to any animal. The invention relates, in particular, to humans, horses, cats (e.g. *Felis domesticus*, the domestic cat) and most preferably to dogs (e.g. *Canis domesticus*, the domestic dog).

The foodstuff of the invention may be a dry product (with approximately 5 to 12% moisture), a semi-moist product (with approximately 12 to 70% moisture) or a wet product (with approximately 70 to 90% moisture).

The foodstuff according to the present invention encompasses any product that a animal consumes in its diet. In particular, the product is a pet food, more particularly a cat or a dog food. Thus, the invention covers standard food products as well as pet food snacks (for example, snack bars, biscuits and sweet products). The foodstuff is preferably a cooked product. It may incorporate meat or animal derived material (such as beef, chicken, turkey, lamb, fish, blood plasma, marrow bone etc or one or more thereof). The product alternatively may be meat free (preferably including a meat substitute such as soya, maize gluten or a soya product) in order to provide a protein source. The product may contain additional protein sources such as soya protein concentrate, milk proteins, gluten etc. Preferably, the protein source is a selected protein such as one or more of chicken, rice, catfish, capelin, tapioca or mehaden. For the purposes of this invention, a selected protein is a protein derived from a minimum number of ingredients, where the ingredients are not commonly associated with sensitivity reactions.

The product may also contain a starch source such as one or more grains (e.g. corn, rice, oats, barley etc), or may be starch free. It may include a gelatinised starch matrix.

The foodstuff is preferably packaged. In this way, the consumer is able to identify, from the packaging, the ingredients in the foodstuff and confirm that it is suitable for the particular pet in question. The packaging may be metal (usually in the form of a tin or flexifoil), plastic (usually in the form of a pouch or bottle), paper or card. The amount of moisture in any product may influence the type of packaging, which can be used or is required.

The foodstuff of the invention is preferably a complete and balanced food or is preferably used in combination with a complete and balanced food (for example, as described in National Research Council, 1985, Nutritional Requirements for Dogs, National Academy Press, Washington D.C. or Association of American Feed Control Officials, Official Publication 1996). A complete and balanced diet includes a high quality commercial food. A high quality commercial food can be defined as a diet manufactured to the nutrient recommendations of the National Research Council, 1985 (supra), wherein the digestibility of key nutrients is 80% or more.

The concentrations of the components to be added to the foodstuff are calculated on the basis of the energy content of the foodstuff and of any additional nutrients which may be consumed by the animal. Preferably, a complete and balanced food, (including a high quality commercial food) comprises the foodstuff according to the invention.

The foodstuff of the first aspect can be provided as a food supplement. The food supplement can be a powder, biscuit, kibble, sauce, topping, pocket or tablet that can be administered with or without an additional foodstuff. Where the food supplement is administered with an additional foodstuff, the food supplement can be administered sequentially simultaneously or separately. The food supplement may be mixed with the foodstuff, sprinkled or poured over the foodstuff or served separately. Alternatively, the food supplement can be added to a liquid provided for drinking such as water or milk.

The second aspect of the invention relates to a foodstuff of the first aspect for use in medicine. In particular, the foodstuff is for use in controlling a skin disorder.

For the purposes of this invention, the terms "control" and "controlling" mean to decrease or alleviate the symptoms suffered by an animal especially the symptoms of a skin disorder and/or assist in the management of a skin disorder. The terms "control" and "controlling" further mean to promote or aid recovery of the skin for example to improve the appearance and condition of the skin during or after conventional treatment. Preferably this foodstuff is provided as an adjunct therapy and is preferably provided in combination with a conventional treatment. Such conventional treatment may include the administration of a medicament such as a steroid, such as prednisolone and/or hydrocortisone. The conventional treatment may further involve the administration of a medicament by any convenient method including orally (including by inhalation), parenteral, mucosal (such as buccal, sublingual, nasal), rectal, transdermal or topical.

The conventional treatment may involve a topical treatment such as a shampoo, humectant or occlusive. Shampoos (such as Hibiscrub) may remove debris and may alleviate the pruritus for a few hours. Common ingredients for topical shampoos include coal tar, benzoyl peroxide, selenium sulphide and Ketoconazole. Regular use of antimicrobial shampoos may help control secondary pyoderma. Topical therapy with humectants and/or occlusives may help to maintain epidermal barrier hydration and inhibit water loss. In dogs susceptible to atopy and/or flea allergy, ectoparasites, particularly fleas or scabies, must be rigorously controlled as they will provoke pruritic responses that quickly breach the pruritic threshold. Fleas can be treated with products such as Stronghold™ (Selamectin), Advantage™ (Imadoclopramid), Program™ (Lufenurun), Frontline™ (Fipronil) or organophosphate derived treatments. Scabies may be treated with Aludex™.

Secondary bacterial infections (for example Staphylococci) commonly occur on atopic skin. Such secondary pyoderma is the most common reason for a stable atopic to exhibit increased pruritus. Overt bacterial infection may be treated topically with Hibiscrub, systemically with antibiotic tablets, or with both systemic and topical treatments. Malassezial (for example *Malassezia pachydermatis*) infections are associated with increased pruritus. Topical antimalassezial shampoos (containing miconazole and/or Ketoconazole) are often useful in controlling secondary malassezial dermatitis.

Atopy is a common cause of *otitis externa* and in such cases controlling the underlying atopy may help. Often symptomatic topical therapy is also required. In some cases severe secondary changes, accompanied with thickening of skin causing closure of the ear canal, may require surgery, such as lateral wall resection or vertical canal ablation.

Symptomatic relief of dogs perennially affected with pruritus can be achieved with immunotherapy. This is obtained by administering a course of injections, usually at monthly intervals, and can take up to six or eight months. During the period of induction it may be necessary to administer low-dose (0.2-0.5 mg/kg) glucocorticoids, for example, alternate day prednisolone, prednisone or methylprednisolone (PPMP). Symptomatic control of pruritus with PPMP, antihistamines or poly-unsaturated fatty acids may be indicated in, 1) the control of pruritus pending induction of remission with immunotherapy and 2) the control of pruritus in the 60% of dogs that fail to achieve remission with immunotherapy (including also those cases where immunotherapy has not been elected).

The use of antihistamines to control atopy in dogs is continually being re-evaluated, but failure of one type of antihistamine does not necessarily mean failure of this course of action. Typical antihistamines include Clemastine, Chlorpheniramine and hydroxyzine.

Identification of the allergen/s that are the cause of the underlying condition and feeding that allergen to desensitise the dog, may also be an effective treatment for atopy, or allergies. Unfortunately, the identification of the allergens can sometimes be inconclusive and desensitisation is not 100% successful. But with allergy orientated diseases, treatment of the underlying cause of the disease is more effective than treating the symptoms.

The foodstuff of the invention may allow the reliance on a conventional treatments such as drug or immuno-therapy to be reduced. Alternatively the animal may exhibit less symptoms or the severity of the symptoms may be reduced. The animal may exhibit an improved level of well being.

The skin disorder may be an inflammatory or allergic skin disorder. The inflammatory or allergic skin disorder may include one or more of atopy, flea allergic dermatitis, contact allergy, dermatitis, pruritus, alopecia, food sensitivity (especially food sensitivity manifesting as a dermatological disorder) or inflammation. The foodstuff of the first aspect is also used for controlling conditions resulting from the skin disorder such as skin irritation, dermatitis and excessive hair loss.

Disorders such as inflammatory or allergic skin disorders can be complicated by the occurrence of secondary infections caused by bacteria or yeasts. Thus the second aspect of the invention further relates to a foodstuff of the invention for use in controlling a bacterial infection associated with a skin disorder in particular in association with an inflammatory or allergic skin disorder.

Furthermore, the foodstuff of the first aspect assists in the promotion and/or maintenance of skin health. Thus, the foodstuff will provide the necessary components for rebuilding and maintaining the skin structure.

The foodstuff of the first aspect can provide benefits to an animal with a skin disorder by reducing itching, reducing the risk of infections and reducing the severity of inflammation, which can be associated with a skin disease or disorder. Furthermore, the foodstuff can enhance and promote the recovery of the skin. In particular, the foodstuff can promote and/or aid recovery from skin diseases such as atopic and/or allergic skin diseases and secondary infections associated therewith. In particular, the foodstuff can aid recovery of skin trauma associated with itching and the resulting damage due to scratching, skin abrasions, inflammation and bacterial infections. The foodstuff may further provide an enhancement and optimization of skin barrier function.

The foodstuff of the first aspect may be provided as a commercial product, which will be available from commercial outlets and/or from veterinary surgeons.

In a preferred feature of the second aspect, the foodstuff of the first aspect will be provided as required, under the direction of a veterinary surgeon. The foodstuff will preferably be fed in combination with one or more specific treatments for a skin disorder under the guidance of a veterinary surgeon. The foodstuff will preferably be branded as a dietary aid, or complete foodstuff and preferably not as a medicament.

All preferred features of the first aspect of the invention also apply to the second aspect.

The third aspect of the invention relates to the use of vitamin C, taurine, curcumin and *aloe vera* in the manufacture of a composition for the control of a skin disorder. The third aspect of the invention may further involve the additional use of one or more of zinc, vitamin A or one or more fatty acids in the manufacture of a composition for the prevention or treatment of a skin disorder. In a preferred feature of the third aspect, the composition is a foodstuff.

All preferred features of the first and second aspects, also apply to the third aspect.

The fourth aspect of the invention comprises a method of controlling a skin disorder comprising administering a foodstuff of the first aspect to an animal. The animal may be in need thereof. Preferably, the animal is suffering from or has a predisposition to one or more of atopy, FAD, contact dermititis, pruritis, alopecia, inflammatory skin condition and food sensitivity and/or one or more secondary infection associated with one or more of the above conditions.

For the purposes of the fourth aspect, the foodstuff is administered daily or twice daily. The foodstuff can be administered in combination with or in place of the animal's conventional food. The foodstuff is provided as an adjunct therapy and is preferably provided in combination with a conventional therapy. For the purposes of this invention, the foodstuff can be provided with the conventional therapy to control the skin disorder. Additionally, the foodstuff can be provided after the course of conventional therapy has ended, in order to promote or aid the recovery of the skin by for example, aiding recovery of skin lesions, skin abrasions, skin trauma associated with itching, damage due to scratching, inflammation etc.

All preferred features of the first, second and third aspects of the invention also relate to the fourth aspect.

The fifth aspect comprises a process for the preparation of the foodstuff of the first or second aspects.

The foodstuff can be made according to any method known in the art such as in Waltham Book of Dog and Cat Nutrition, Ed. ATB Edney, Chapter by A. Rainbird, entitled "A Balanced Diet" in pages 57 to 74 Pergamon Press Oxford.

The components are added together at any time during the processing. They may all be added together at the same time, or individually, in any particular order. Other ingredients of the foodstuff may be added at any time during the processing. Preferably, two or more ingredients of the foodstuff are mixed together and then ground together. The moisture and temperature of the ground particles can be manipulated prior to any further processing step. The components may be added before or after any heating or cooking step. The processing may include shaping and/or packaging of the product. In a preferred feature of the fifth aspect, the product is shaped by extrusion to form pellets or kibbles. Extrusion preferably occurs at a pressure of 20-1000 psig and a temperature of 90-165° C.

The components of the foodstuff (for example, *aloe vera*, taurine, curcumin or vitamin C) may be mixed with the other components of the foodstuff or can be added to the completed foodstuff. In a preferred feature of the invention, one or more of the components (for example *aloe vera*, taurine, curcumin or vitamin C, preferably *aloe vera*) is coated or sprayed on to the surface of the foodstuff. Alternatively, one or more components comprising *aloe vera*, vitamin C, taurine or curcumin are admixed, with one or more other components of the foodstuff. The final water content of the foodstuff can be manipulated using a cooler apparatus.

All preferred features of the first, second, third and fourth aspects, also apply to the fifth aspect.

BRIEF DESCRIPTION OF THE DRAWINGS

The invention is illustrated by reference to the following figures:

FIG. 1 shows a comparison of plasma vitamin C after incubation of dogs with a control and the foodstuff.

FIG. 2 shows a comparison of plasma taurine after incubation of dogs with a control and the foodstuff.

FIG. 3 shows the effect of the foodstuff and the control on the rate of diffusion of radiolabelled water across an in vitro skin barrier.

FIG. 4 shows the effect of the foodstuff on Keratinocyte skin lipid production.

FIG. 6 shows the effect of the foodstuff on skin recovery.

FIG. 7 shows the effect of the partial foodstuff and the full foodstuff on skin recovery.

FIG. 8 shows the bacteriocidal effect of the foodstuff on the skin isolate SCO6.

FIG. 9 shows the bacteriocidal effect of the foodstuff on the skin isolates SCO1, SCO7 and SC08.

FIG. 10 shows the anti-inflammatory effect of the foodstuff on fibroblasts.

DETAILED DESCRIPTION OF THE INVENTION

Figure 5:
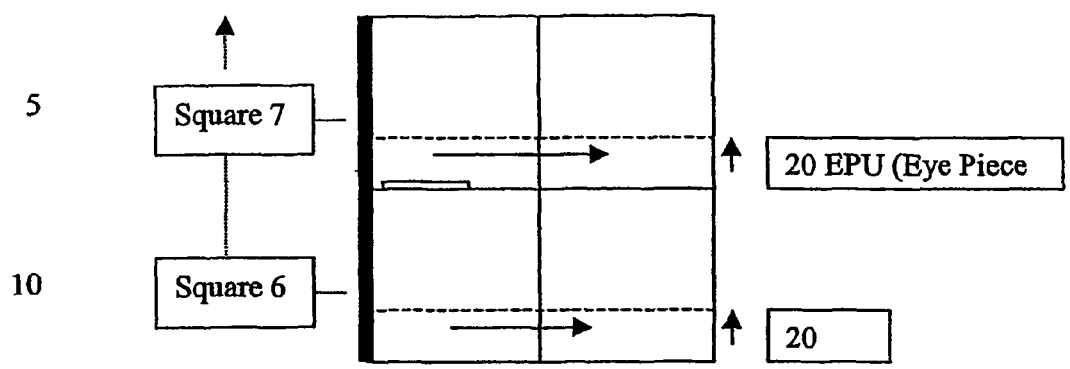
FIG. 5 shows the positioning of a dish on the for counting of stained cell nuclei.

The invention will now be illustrated by reference to the following non-limiting examples.

EXAMPLES

Example of Skin Diet

This skin diet provides between approximately 310 and 350 kcal/100 g. The skin diet is a dry diet containing approximately 10% water. The skin diet comprises the following ingredients:

| | |
|---|---|
| Rice | ~58% |
| Fish meal | ~30% |
| Fibre | ~5% |
| Vitamins and minerals (including Vitamin C ~1.25%) | ~6% |
| Corn oil | ~4% |
| Taurine | ~0.5% |
| Curcumin | ~0.5% |
| Aloe vera | ~0.06% |

Dry raw materials are weighed, mixed and ground. The dry mix is then screened prior to extrusion to form the mixed meal. The mixed meal is conveyed to a pre-conditioner where it is mixed with steam, water and oil at specified rates. Sufficient residence time is provided in the pre-conditioner for the moisture and temperature to transfer uniformly throughout the individual particles. The residence time is about two minutes. The pre-conditioned mixture is then transferred to an extruder for cooking and forming. The die pressure should be 200-1000 psig and the die temperature is about 90-165° C. The formed kibble is pneumatically conveyed to the dryer. The drying temperature is set at 130-145° C. and drying time is about 17 minutes. The product moisture exiting the dryer should be less than 12%. The dried kibble is sized (or screened) before coating to reduce clumps and fines. The kibble is fed into a coating system where coating is applied uniformly across the surface of the kibble at a constant application rate. The coating materials include digest and a mixture of *Aloe Vera* Extract powder and oil. The *Aloe* powder/oil mixture is prepared by dispersing an accurate amount of *Aloe Vera* Extract powder into a fixed amount of oil. The mixture must be well mixed, i.e., all *Aloe* powder is uniformly dispersed in the oil, prior to application. The kibble is coated with the *Aloe* powder/oil mixture first followed by digest at ambient temperature. The coated kibble is then transferred to a post-coat cooler in which the coated product is conditioned to its final moisture (<12%), water activity (<0.7 at 35° C.) and temperature (<35° C.) prior to packaging. The retention time is about 15 minutes.

Effect of Foodstuff on Dogs.

A panel of dogs underwent a feeding trial to compare the effects of feeding the foodstuff with a control diet. The control diet contained the same ingredients as the foodstuff minus vitamin C, curcumin, taurine and *aloe vera*. The dogs fed with the foodstuff showed a benefit compared to those on the control diet. Further, no deleterious side effects were observed with the foodstuff.

Determination of the Effect of Curcumin Supplemented Diets on Cats.

The study was carried out using eight cats which were known to be in good intestinal health. Cats were wormed and vaccinated 6 months prior to the start of the trial.

The cats underwent the following trial regime;

| | |
|---|---|
| 14 days | Control diet |
| 28 days | Curcumin enriched diet |
| 14 days | Control diet |

Both the control diet and the curcumin enriched diet provided 405 kCal/100 g. The control diet was a dry diet containing approximately 4% water. The control diet comprised the following ingredients:

| | |
|---|---|
| Poultry | ~37% |
| Beef Tallow | ~10% |
| Rice | ~20% |
| Maize meal and gluten | ~26% |
| Sunflower oil | ~3% |
| Brewers yeast and vitamins | ~3% |

The curcumin-supplemented diet comprised 0.5% by weight curcumin. The curcumin was sprayed onto the external surface of the dry control product.

Measurement of Immunoglobulin Levels

Blood samples were taken and serum was prepared. The serum was aliquoted and frozen at −20° C. until required. Levels of immunoglobulins were measured by radial immunodiffusion (RID, Bethyl), a procedure for the quantitation of specific proteins based on an antigen-antibody reaction occurring in a support medium (agarose gel) and visualised as an opaque precipitin ring. Antigen concentration can be determined by relating the log of the concentration to the precipitin ring diameter. In brief, 10 ul serum samples and standards (5 ul for Ig G) transferred to middle of RID plates specific for feline Ig G, Ig A, and Ig M. The plates were incubated for 3 days and the diameter of the precipitin ring measured using a RID reader. A standard curve was constructed by plotting the log concentration of standard against precipitin ring diameter, and the concentration of the test samples calculated using the regression equation obtained.

Measurement of Serum Nitric Oxide

Serum NO was determined by the Griess reaction. Griess reaction tests were obtained from Promega and performed as described in the provided protocol sheets. In brief, 50 µl of serum sample and NO standard (diluted in FCS) was added in duplicate to wells in a 96 well plate. 50 µl of Sulphanilamide solution was dispensed to each well and the plate incubated in the dark at RT° for 5-10 minutes. After incubation 50 µl of NED solution was added to each well and again incubated in the dark for 5-10 minutes at RT°. The optical density of each well was determined immediately using a microplate reader set between 520 and 550 nm. Serum nitric oxide concentration (uM) was calculated from a standard curve.

Immunoglobulin Levels in the Serum of the Cats

| Ig levels in the serum of cats (mg/dl). | | |
|---|---|---|
| Diet | Control | Supplemented |
| Ig G | 15.10 ± 2.63 a | 14.39 ± 3.65 a |
| Ig M | 1.85 ± 0.67 a | 1.38 ± 0.63 b |
| Ig A | 0.28 ± 0.07 a | 0.27 ± 0.10 a |

Same letter denotes no significant difference ($p > 0.05$).

Serum Nitric Oxide Concentration in Cats

| Serum NO | |
|---|---|
| Diet | Mean NO (υM) ± SD |
| Control | 26.7 ± 15.0 a |
| Supplemented | 18.3 ± 6.18 ab |

Same letter denotes no significant difference ($p > 0.05$).

Determination of the Effect of Vitamin C Supplemented Diets on Dogs.

Trials in dogs have shown that feeding vitamin C supplemented foodstuffs (with vitamin C at levels of 40 mg per 400 kcal) increases the antioxidant status of the animals and contributes to increased health benefit.

Effect of Foodstuff on Circulating Vitamin C and Taurine Levels in Blood Plasma

Methods

The study was carried out using 20 small breed dogs (i.e. Miniature Schnauzer, Cairn terrier, cocker spaniel, poodle or west highland white). Dogs were age/sex matched and fed individually in their pens during the trial. Room temperature was maintained at 22° C. with a natural daylight cycle.

For the first 16 days of the trial all the dogs were fed on a control diet and experimental procedures performed to complete the washout phase. Before the start of the first test phase, the dogs were split into a test group and a control group containing equal numbers of dogs that were age/sex matched and with each group showing an equal mean dental score.

During the trial all dogs were fed to their respective needs for adult maintenance of body weight. This required food intake and body weight to be measured throughout the trial.

During the first phase, the test group were fed for 9 weeks on a control diet with curcumin (500 mg/400 kcal), *aloe vera* (70 mg/400 kcal) Vitamin C (350 mg/400 kcal) and Taurine (500 mg/400 kcal) added on top of the diet. The control group were fed control diet only.

After a washout phase, the second test phase was carried out.

Further experimental procedures were performed at the end of $1^{st}$ test phase after which point the groups were crossed over. Further experimental procedures were performed at the end of the washout phase and at the end of the $2^{nd}$ test phase.

Blood samples were collected from each dog during week 1 and at the end of each study phase. 10 ml (total) of blood was collected by syringe hypodermic needle. See Table 1.

TABLE 1

Collection of Blood

| Blood volume (ml) | Collection Vessel | Purpose for collection |
| --- | --- | --- |
| 1 | Non Anticoagulant | RID Serum Ig E, Ig G, Ig M |
| 2.5 | EDTA | APP, E-toxin, Haem, WBC, Lip Perox PGE1, 2, LK B4 |
| 1.8 | Lith Hep | Biochem |
| 5 | Lith Hep | Taurine, vit C, aloin, man-6-phos, histamine, curcumin. |

PGE = Prostaglandin,
Ig = Immunoglobulin,
APP = Acute Phase Protein,
WBC = White Blood Cell,
FACS = Fluorescent Activated Cell Sorting,
E-Toxin = Endo-Toxin,
Lip Perox = lipid peroxidation (plasma),
LK = Leukotriene,
EDTA = Eyhylenediaminetetra acetic acid,
RID = Radial Immunodiffusion.

Results for this study are indicated in FIGS. 1 and 2. At the end of each test phase the mean levels of circulating Vitamin C and taurine in the test groups were higher than in the control groups that were not supplemented. This data indicates that by feeding the foodstuff, the antioxidant, antibacterial, and recovery capabilities of the dog can be increased.

Improved Barrier Function: Diffusion Assay

This assay demonstrates the effect of the foodstuff comprising Vitamin C, Taurine, *Aloe* Vera and Curcumin, on improving barrier function, as assessed by use of the diffusion assay. The rate of diffusion of radiolabelled water across an in vitro skin barrier (composed of canine keratinocyte skin cells) was compared in cells cultured both in the presence and absence of the foodstuff.

Methods

Costar Snapwell plates (ASL Cat No. 402/0369/08) were set up containing 2.6 ml Greens media in the outer well and 400 µl Greens in the inner well, the latter was seeded with canine keratinocytes at $1 \times 10^5$. These plates were incubated at 37° C., 5% $CO_2$. The Greens media in the inner well was changed the following day to remove any dead cells. These plates were cultured for a further two days. Greens media was prepared containing test concentrations of foodstuff (10 µl/ml). Control media was also prepared containing DMSO (10 µl/ml). On day four the media was removed from the inner and outer wells and 900 µl of test/control media was replaced into the outer well. Two snapwells were used per concentration of foodstuff and one control was used per plate. This low level of media ensures that the keratinocytes are at the air-liquid interface. These plates were cultured for a further seven days the media was replaced every two-three days. On day 11 the snapwells were ready for the diffusion assay. The inner well of each snapwell was removed and placed into individual diffusion chambers. Dulbecco's Modified Eagle's Medium (DMEM) was added to both sides of the chamber (6 ml per side), each chamber was then placed into the diffusion apparatus. This equilibrates the chambers to 37° C. and enables gas (5% $CO_2$ in air) to be continuously pumped through the chambers thus ensuring movement of the media. 100 µl of radiolabelled water (3H) was added to the left-hand side of each chamber and 50 µl samples were taken for 90 minutes at three-minute intervals from the right hand side. DMEM (50 µl) was replaced into the right hand side after each sample. Samples were placed into scintillation vials containing 4 mls scintillation fluid and the amount of radioactive label in each sample was counted using a scintillation counter.

The results for this assay are indicated in FIG. 3. The rate of diffusion across the skin barrier has been reduced in cells cultured in the presence of the foodstuff. This data suggests that incubation of the cells in the presence of the foodstuff reduces trans-epidermal water loss through the skin surface (as indicated by a decreased rate of diffusion). This data shows that the foodstuff promotes the formation and optimisation of a functional skin barrier.

Improved Skin Barrier: Lamellar Lipid/Ceramide Synthesis Assay

The ability of canine keratinocyte skin cells to synthesise ceramide, a lamellar lipid, was compared in cells cultured both in the presence and absence of the foodstuff. Increased synthesis of ceramides improve the stratified layer of the skin thereby improving the barrier function of the skin. Ceramide synthesis was directly assessed through measuring the levels of $^{14}C$-Serine incorporation.

Methods

Canine keratinocytes were seeded in MCDB 153 media (see contents below) into collagen coated 24 well plates (Sigma, Cat No.Z38,049-0) at a cell density of $5 \times 10^4$ per well. These plates were incubated at 37° C., 5% $CO_2$. The following day the media was changed on each well to remove any dead cells. On day four of incubation the media was changed again (500 µl of MCDB 153 without BPE). Foodstuff was then added at varying test concentrations (10 µl/ml), DMSO was added to the control wells (10 µl/ml), six wells were used per test/control. Plates were incubated with these supplements for a further five days, the media and supplements were replaced once during this period. On day five the media and supplements were again replaced and 5 μl of 14C-Serine added to each well. These plates were incubated and harvested with trypsin on day 12. Each well was harvested individually and the pellet stored at −20° C. The incorporation of 14C Serine was measured in each cell pellet using Bligh-Dyer solvents. The cell pellets were defrosted and 300 μl Bligh-Dyer solvent added to each pellet (Chloroform 10 ml, Methanol 5 ml, de-ionised water 1 ml and 1 ml 0.88% KCL). This solution was mixed for 20 seconds using a motorised pellet pestle. The samples were then spun at 1300 rpm for 3 minutes to facilitate the separation of the layers. The bottom layer of each sample (containing the radiolabelled lipid) was then carefully removed and added to scintillation vials containing 4 mls scintillation fluid. The amount of 14C-serine in each sample was then measured on a scintillation counter.

The results of this study are shown in FIG. 4.

MCDB 153 Recipe

MCDB 153 (Sigma # M7403).

Supplemented with Insulin (5 mg/L), Hydrocortisone (180 mg/L), 2-aminoethanol (6.1 mg/L), O-phosphorylethanolamine (14.1 mg/L), epidermal growth factor (100 ng/L) and Bovine pituitary extract (0.4% v/v).

Insulin. Sigma #I6634
Hydrocortisone. Sigma # H0396
2-aminoethanol. Sigma # E0135
O-phosphorylethanolamine. Sigma # P0503
Epidermal Growth Factor. Sigma # E4127
Bovine Pituitary Extract. Sigma # P1476/Invitrogen #13028-014

Conclusions

The level of ceramide synthesis in the skin is increased in cells, which have been cultured in the presence of the foodstuff. This data suggests that incubation of the cells in the presence of the foodstuff could improve barrier function through increasing the level of lamellar lipid synthesis and thus helps to create skin with improved barrier function. In turn this will prevent the perfusion of pathogens or allergens through the skin which could lead to infection or allergy, respectively.

Skin Recovery Assay

This assay determine the effect of the foodstuff (Vitamin C, Taurine, *Aloe* Vera, Curcumin) on improving skin recovery in an in vitro wound scenario as investigated by use of skin recovery assay. The ability of canine dermal fibroblast cells to migrate, post-wounding, was compared in cells cultured both in the presence and absence of the foodstuff.

Method

On day 1 of this experiment, tissue culture dishes (with lid and vent, sterile, 35 mm×10 mm, 2×2 mm grid, 174926 Nalge Nunc international) were used with a line drawn on the underside of each dish approximately down the centre line to represent the wound line. Two dishes were allocated as control and two for the test experiments. The dishes were then seeded with canine dermal fibroblasts (approximately $4 \times 10^5$ per dish in 2 ml of fibroblast media) and incubated overnight at 37° C.

On day two, the tissue culture dishes were checked for confluency using a phase contrast microscope. Media was removed from the plate (1 ml) to aid in scraping and each plate was scraped of cells from the wound line over half the plate using a Cell Scraper (Nunc 179693, 23 cm). To insure that half the cells had been removed from the plate they were viewed again under the phase contrast microscope. The remaining media was removed and the cells were then washed with 1 ml of fibroblast media. A further 2 mls of Fibroblast media+20 μl of DMSO (control) or Test substance (foodstuff) was added and the cells were incubated at 37° C. for 48 hours.

After this period the media was removed from each plate and the same concentrations were pooled for analysis of $PGE_2$ synthesis. The dishes were removed from the incubator and washed with PBS (1 ml). 70% methanol (1 ml) was added to each dish and left for 10 minutes in order to fix the cells. Again the cells were washed with 1 ml PBS. After this the cells were bathed for 1 hour in approximately 1 ml of a 1 in 5 dilution of Giemsa Stain (Sigma, 028H4351) in sterile water that had been filter sterilized. The cells were washed in PBS and stored in the fridge until ready for counting.

For counting purposes each dish was positioned on the phase contrast microscope with the 'wound' to the right-hand side.

As illustrated in FIG. 5, on the sixth to the eleventh squares up, the stained cell nuclei were counted in the 20 eye piece units. The number of cells per square for all six squares were recorded in order to calculate the average. This was then repeated with all plates stained. (N.B Counting of plates was undertaken without prior knowledge of the concentration of foodstuff added.)

The results for this study are shown in FIG. 6.

Conclusions

The number of cells that migrated into the denuded space created by the wounding procedure was increased in cells cultured in the presence of the foodstuff. This data shows that incubation of the cells in the presence of the foodstuff promotes skin recovery, possibly through promoting cell migration and or/cell proliferation. Thus helping to create skin with improved barrier function and greater potential for recovery after injury or disease.

The skin recovery assay was then carried out as discussed above in order to compare the effect of the foodstuff (Vitamin C, Taurine, *Aloe* Vera, Curcumin) on a control foodstuff and on a partial foodstuff (Vitamin C and Taurine). The canine dermal fibroblasts were cultured on plastic and then half of the confluent monolayer was removed with a cell scraper. Both partial and full foodstuff were present at 0.125 mg/ml.

The results as illustrated in FIG. 7, show that the partial foodstuff improves the recovery rate of the fibroblasts growing in the monolayer. However the full foodstuff provides a much greater benefit from the partial foodstuff, and has the greatest potential to stimulate the migration and proliferation of cells into the denuded space on the plastic. Full foodstuff therefore shows a greater benefit in improving skin recovery after disease or injury than a partial foodstuff containing Vitamin C and taurine.

| | | | Bacteriology Assays | | | | |
|---|---|---|---|---|---|---|---|
| Foodstuff conc mg/ml | Time pts hrs | Strains used | Shaking | Temp C. | No. of runs | Established growth | DMSO volume/ml |
| 1 | 6, 24 | E. coli, staph, sco1–sco8 | N | 38 | 2 | Y | — |

-continued

| Bacteriology Assays | | | | | | | |
|---|---|---|---|---|---|---|---|
| 1 | 6, 24 | E. coli, staph, sco1–sco8 | N | 38 | 1 | Y | 1 |
| 10 | 24 | E. coli, staph, sco1–sco8 | N | 38 | 1 | Y | — |
| 5 | 6, 24 | E. coli, staph, sco1–sco8 | Y | 38 | 1 | Y | 0.5 |
| 5 | 6, 24 | E. coli, staph, sco1–sco8 | N | 38 | 1 | Y | 0.5 |
| 5 | 6, 24 | E. coli, staph, sco1–sco8 | Y | 24 | 1 | Y | 0.5 |
| 0.5 | 6, 24 | E. coli, staph, sco1–sco8 | Y | 38 | 3 | Y | 0.05 |

| Bacterial strains used | |
|---|---|
| Code | Strain |
| SC01 | *Exiguobacterium* species (species level match) |
| SC02 | *Staphlococcus intermedius* (species level match) |
| SC03 | *Bacillus licheniformis* (species level match) |
| SC04 | *Bacillus pumilus* (species level match) |
| SC05 | *Macrococcus caseolyticus* (genus level match) |
| SC06 | *Neisseria canis* (species level match) |
| SC07 | *Psychrobacter phenylpyruvicus* (species level match) |
| SC08 | *Macrococcus caseolyticus* (species level match) |
| SK01 | *E. coli* |
| SK02 | *Staphlococcus intermedius* |
| SK03 | *Propionibacterium acnes* |

Strains SC01-SC08 were isolated from dog skin and coat. All the samples were taken from healthy dogs with no obverse skin conditions and then sequenced by NCIMB:

SC01: *Exiguobacterium* Species

Formerly known as *Corynebacterium* species and belong to the family of Coryneform bacteria. The species associated with infections are *E. acetyliticum* and *E. auranticicum*. A number of clinically reported strains have been isolated from various sources e.g. skin, wounds and cerebrospinal fluid. They are motile by peritrichous flagella, facultatively anaerobic with fermentative carbohydrate metabolism.

SC02: *Staphylococcus intermedius*

They are normal inhabitants of the skin and hair surface, and mucous membranes. However *Staphylococcus intermedius* is the most frequently isolate from the lesions of canine pyoderma.

They are gram positive cocci, facultative anaerobes and are increasingly becoming associated (as opportunistic pathogens) with serious infections. It also has growing prevalence of resistance to many antibiotics.

SC03: *Bacillus licheniformis*

It is a Gram-positive, motile, spore-forming facultatively anaerobic rod. Food poisoning caused by *Bacillus licheniformis* is characterised by diarrhoea, although vomiting occurs in half of reported cases. The food poisoning has been associated with cooked meat, poultry and vegetable dishes (particularly meals served with rice).

SC04: *Bacillus pumilus*

It is a gram-positive, motile, facultatively anaerobic rod. Food poisoning caused by *Bacillus pumilus* is characterised by vomiting and diarrhoea. The food poisoning has been associated with meat pie's, eggs, cheese and fruit juice.

*Bacillus pumilus* and its metabolites have been suggested to have antibacterial properties and have the potential as a biocontrol agent of moulds and mycotoxins in cereal grains and food commodities.

SC05: *Macrococcus caseolyticus*

It is a gram-positive, coccoid, non-motile, not capsulated, facultative anaerobe but with a strong preference towards aerobic conditions. The optimum growth temperature is 35° C. It has a positive reaction for catalyse and oxidase.

No pathogenicity has been reported to be linked to Macrococcus caseolyticus. It has been reported to be isolated from bovine milk and animals SC06: *Neisseria canis*

Nearly all species of *Neisseria* are aerobic gram-negative diplococci. They are cytochrome oxidase and catalase positive and non-fastidious. They have optimal growth in a moist atmosphere. The natural habitat of *Neisseria* species is the mucous membranes of the respiratory tracts of warm-blooded animals. *Neisseria canis* has been isolated from the throats of dogs and cats and has been reported to cause infection in cat and dog bite wounds of humans.

SC07: *Psychrobacter phenylpyruvicus*

*Psychrobacter*—a proposed genus to be included in the family *Neisseriaceae*. They are short gram-negative rods, most often occurring as diplobacilli. They are nonmotile, non-endospores. The optimal temperature for growth is 33 to 37° C. Strains are aerobic, catalase and oxidase positive. Strains have been isolated from genitourinary tract, blood, cerebrospinal fluid and pus of various lesions. Species associated with infection, *P. immobilis* and *P. phenylpyruvicus*. Associated infections, meningitis, bacteraemia and eye infections.

SC08: *Macrococcus caseolyticus*

Same as SCO5

SK001: *E. coli*

*E. coli* is a gram-negative, aerobe. Optimal growth temperature is 37° C. It is one of the most common inhabitants of the intestinal tract and skin flora. Generally most species are not considered pathogenic, however can cause disease under certain conditions. Pathogenic strains can cause food poisoning associated with diarrhoea or other serious infections.

SK02: *Staphylococcus intermedius*

Same as SC02

SK03: *Propionibacterium acnes*

*Propionibacterium acnes* are widely distributed on human skin, hair, oropharynx, gastrointestinal tract and is considered to cause skin disorders and acne. It is a gram-positive, non-spore forming anaerobic rod. The organism is found on the oily areas of the skin such as the scalp and forehead. It is thought that *P. acnes* is a member of the normal canine microflora which can be transferred to man. The distribution of the organism was found to be similar to that found on man, however the organism appears to be well adapted to the dog and in not thought to be associated with any canine dermatoses (Muller et al 1989).

It has also been reported that *P. acnes* may protect against cancer by promoting the TH-1 type immune response (Anne Eady, 2002).

Inhibition of Bacteria by the Foodstuff in Broth Culture

1) Sub strains *E. coli*, Staph I, SC01-SC08 on to BHI agar plates and incubate 38° C. overnight.

2) Next Day add 1 colony of bacteria into 10 mls BHI broth for each strain and incubate 38° C. statically.

3) The foodstuff is made up of the following ingredients Vitamin C, Taurine, *Aloe vera* and Curcumin as outlined below, in 50 ml BHI broth at 1 mg of foodstuff/1 ml BHI broth. This is then vigorously votexed and then incubated 38° C.

4) After 3 hrs perform 10 fold serial dilutions and make a growth indicator plate (see below).

5) Split each of the bacterial broths for each strain into two, 5 ml in a new tube, leaving 5 ml remaining in old tube.

6) Add 5 ml of fresh BHI broth into one of the tubes from stage 4 (control).

7) Add 5 ml of made up foodstuff (1 mg/ml) to the other tube from stage 4 (test).

8) Both tubes (control) and (test) for each strain should contain a final volume of 10 ml. Tubes are then incubated at 38° C.

After 3 hrs indicator plates for both (control) and (test) tubes for each strain are made.

10) Indicator plates are made again after incubating overnight.

Foodstuff

1) Vitamin C: 30 mg/400 kcal

2) Taurine: 500 mg/400 kcal

3) *Aloe vera*: 70 mg/400 kcal

3) Curcumin: 500 mg/400

Concentrations of Foodstuff Tested

The foodstuff was tested at concentrations ranging from 0.1 mg/ml-20 mg/ml. These concentrations correspond to the amount of foodstuff available in the blood after feeding 300 g of the diet per day to an average size dog.

The foodstuff is dissolved in DMSO in order to solubilise the ingredients when incubating the foodstuff with the bacterial.

Conclusions for the Effect of Foodstuff on Bacterial Strains in Broth Culture

Staph I: A small effect in decreasing the growth is observed at 6 hours but not at 24 hours. At 24 hours a slight increase in growth is observed. This indicates that the foodstuff is having a bacteriostatic on Staph I.

SC02: The same is observed as above for Staph I, which suggests repeatable results as SCO2 is also Staph I.

SC06: There is a massive effect of decreasing the growth of SC06 overtime and with different concentrations of the foodstuff. This indicates that the foodstuff is showing bacteriostatic properties, and at 24 hours in some concentrations is it actually showing bactericidal properties. (results as indicated in FIG. 8)

SC01, SC03, SC04, SC05, SC07, SC08 show an average decrease in growth in the presence of the cocktail. FIG. 9 indicates data for SC08, 7 and 1 after 6 hours and 24 hours in culture. The experiments were run in triplicate and using the same methods as described above. The graphs demonstrate an inhibitory effect of all three isolates and indicates that the skin support cocktail will be beneficial in controlling secondary infections.

Anti-Inflammatory Effect of the Foodstuff

With allergic skin conditions such as atopy there is a tendency for an increase in the levels of circulating pro-inflammatory mediators such as Prostaglandin E2 and Leukotriene B4. This leads to an increase inflammation at the atopic sites and this becomes disruptive to the recovery process. This assay investigates the effect of the food supplement on the levels of supernatant PGE2 which is produced by canine dermal fibroblasts.

Methods

For this study cell supernatant was used from the recovery assays described in previous correspondence. The supernatants were then analysed using the methods described in the handbook from R+D Systems for a PGE2 High Sensitivity assay kit (cat no DE2100).

The results of this study are shown in FIG. 10. The results indicate that by adding the foodstuff to the supernatant of fibroblasts cultured in vitro, the levels of the pro-inflammatory PGE2 in the media are reduced. Furthermore this effect has been observed in a dose response manner with 0.125 mg/ml foodstuff showing the greatest inhibitory effect.

This data indicates that by feeding the foodstuff to dogs reduces the levels of circulating PGE2, which is pro-inflammatory and thus reduce the inflammation of the skin during conditions such as atopy, flea allergy, or secondary infection or during recovery from these conditions.

Clinical Trial using Skin Diet on Dogs Suffering from Skin Conditions.

A dachshund (6 years old, female) has suffered from a skin condition for 4 years. A number of treatments were used in the past to alleviate this condition including steroid, anti-histamine, fatty-acids, antibiotics, psychotrophic, elimination diet, shampoo and ear care. Various diets had also been used including fish, meat, chicken and vegetable diets.

The dog was fed on the skin diet for 3 months following a 3 month period on a control diet. During the time the dog was fed on the skin diet, the owner noticed a number of improvements in the condition of the dogs skin including an overall improvement in skin condition, the disappearance of a reddish skin area on the dogs foot and an improvement in a skin lesion on the dogs back. The owner wishes to continue feeding the skin diet to the dog after the trial has ended.

Two dogs were fed on the skin diet for 3 months following a 3 month period on a control diet. Both dogs showed an improvement in their condition with a noticeable reduction in the steroid dosage required. After returning the dogs to a control diet, a dog has had a relapse in skin condition.

What is claimed is:

1. A method of reducing inflammation in a dog or cat in need thereof comprising orally administering to said dog or cat a foodstuff comprising an effective amount of vitamin C, taurine, *aloe vera*, and curcumin, wherein the inflammation is caused by a skin or hair disorder selected from the group consisting of: atopy, a dermatological disorder from food sensitivity, a contact allergy, dermatitis, a flea allergy, pruritus, alopecia, excessive hair loss, or a combination thereof.

2. The method of claim 1, wherein the foodstuff comprises from 20 mg to 500 mg of the vitamin C per 400 kcal of foodstuff, from 100 mg to 1000 mg of the taurine per 400 kcal of foodstuff, from 1 mg to 1000 mg of the *Aloe vera* per 400 kcal of foodstuff, from 100 mg to 1000 mg of the curcumin per 400 kcal of foodstuff.

3. The method of claim 1, wherein said foodstuff further comprises vitamin A.

4. The method of claim 3, wherein said foodstuff comprises from 1000 IU to 10,000 IU of the vitamin A per 400 kcal of foodstuff, from 20 mg to 500 mg of the vitamin C per 400 kcal of foodstuff, from 100 mg to 1000 mg of the taurine per 400 kcal of foodstuff, from 1 mg to 1000 mg of the *Aloe vera* per 400 kcal of foodstuff, from 100 mg to 1000 mg of the curcumin per 400 kcal of foodstuff.

5. The method of claim 1, wherein the foodstuff further comprises a fatty acid selected from the group consisting of eicosapentaenoic acid, docasahexaenoic acid, alpha-linolenic acid, gamma-linolenic acid and combinations thereof.

6. The method of claim 5, comprising from 10 mg to 1000 mg of the fatty acid per 400 kcal of foodstuff, from 20 mg to 500 mg of the vitamin C per 400 kcal of foodstuff, from 100 mg to 1000 mg of the taurine per 400 kcal of foodstuff, from 1 mg to 1000 mg of the *Aloe vera* per 400 kcal of foodstuff, from 100 mg to 1000 mg of the curcumin per 400 kcal of foodstuff.

7. The method of claim 1, wherein the skin disorder is atopy.

8. The method of claim 1, wherein the skin disorder is a contact allergy.

9. The method of claim 1, wherein the skin disorder is a flea allergy.

10. The method of claim 1, wherein the skin disorder is pruritus.

11. The method of claim 1, wherein the skin disorder is selected from the group consisting of alopecia, excessive hair loss, and a combination thereof.

* * * * *

UNITED STATES PATENT AND TRADEMARK OFFICE
CERTIFICATE OF CORRECTION

PATENT NO.         : 8,647,681 B2
APPLICATION NO.    : 10/479065
DATED              : February 11, 2014
INVENTOR(S)        : Markwell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1085 days.

Signed and Sealed this
Twelfth Day of July, 2016

Michelle K. Lee
*Director of the United States Patent and Trademark Office*